United States Patent [19]

Chen

[11] 4,377,582
[45] Mar. 22, 1983

[54] 2-PHENYL-4-[CIS-2,5-DIMETHYL-4-(2-PYRIDINYL)-1-PIPERAZINYL]QUINAZOLINE

[75] Inventor: Ying-Ho Chen, Richmond, Va.

[73] Assignee: A. H. Robins Company, Inc., Richmond, Va.

[21] Appl. No.: 266,257

[22] Filed: May 22, 1981

Related U.S. Application Data

[62] Division of Ser. No. 105,161, Dec. 19, 1979, Pat. No. 4,306,065.

[51] Int. Cl.³ .......................................... A61K 31/505
[52] U.S. Cl. .................................................. 424/251
[58] Field of Search ........................................ 424/251

[56] References Cited

U.S. PATENT DOCUMENTS 3,340,260  9/1967  Blatter ............................... 544/293
3,819,628  6/1974  Simpson ............................ 544/293
3,997,538  12/1976  Alaimo ............................. 544/293

Primary Examiner—Paul M. Coughlan, Jr.

[57] ABSTRACT

Novel hypotensive agents are disclosed which are quinazolines substituted in the 2 and 4 position having the general formula:

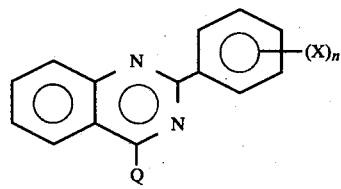

wherein Q is a secondary amine radical illustrated by loweralkanolylamino or a tertiary amine radical such as pyrrolidinyl, piperidinyl or piperazinyl, any of which may be substituted by various groups such as loweralkanolyl.

14 Claims, No Drawings

2-PHENYL-4-[CIS-2,5-DIMETHYL-4-(2-PYRIDINYL)-1-PIPERAZINYL]QUINAZOLINE

This is a division, of application Ser. No. 105,161, filed Dec. 19, 1979, now U.S. Pat. No. 4,306,065.

BACKGROUND OF THE INVENTION

1. Field of Invention

The present invention relates to certain 2-aryl-4-substituted quinazolines, more particularly the invention is concerned with novel 2-arylquinzolines having nitrogen linkage at the 4-position, which compounds have hypotensive pharmacological activity in warm-blooded animals, pharmaceutical methods and compositions.

2. Description of the Prior Art

4-Amino-substituted quinazolines wherein the 4-substituent is a 4-($\beta$-hydroxyethyl)-1-piperazinyl radical or a 4-methyl-1-piperazinyl radical useful as central nervous system stimulants and antidepressants have been disclosed in U.S. Pat. No. 3,470,182. The 2-position on quinazoline is unsubstituted.

4-Phenyl-substituted quinazolines having the 2-position substituted with piperidino or (4-methyl-1-piperazinyl) having analgetic and anti-allergenic activity are disclosed in U.S. Pat. No. 3,505,553.

2-Phenyl-6-hydroxy-quinazolines substituted in the 4-position by piperidino, alkylamino, morpholino and 4-methyl-1-piperazinyl radicals have been reported in Chemical Abstracts 79, 92149n, useful as bactericides.

4-Methylamino-2-(o-nitrophenyl)quinazoline has been disclosed in J. Chem. Soc. 1963, 3062–6. 4-Anilino and 4-(benzylamino)-2-phenylquinazoline have been disclosed in Tetrahedron Lett. 1973 (5) (359–360).

None of the foregoing disclosures reveal hypotensive activity for any of the prior art compounds and none disclose compounds of the present invention.

SUMMARY OF THE INVENTION

The present invention provides novel 2-aryl-4-substituted quinazolines which have important pharmacological activity as hypotensive agents in warm-blooded animals. The compounds of the invention are represented by the following structure formula:

Formula I

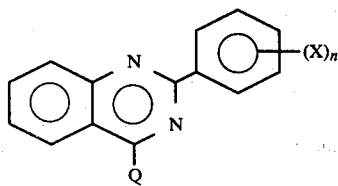

wherein
Q is represented by

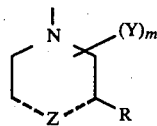

or $-NR_3R_4$

R is selected from hydrogen, hydroxy, loweralkoxy, loweralkanolyl, phenoxy or phenoxy substituted by loweralkyl, loweralkoxy, trifluoromethyl, amino, nitro or halo, Z is selected from

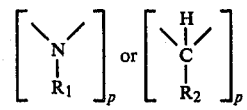

and
p is zero or one;

$R_1$ is selected from loweralkyl, loweralkanolyl, 2-pyridyl, loweralkenyloxy-loweralkanolyl, loweralkynyloxy-loweralkanolyl, loweralkanyloxy-loweralkanolyl, phenoxy-loweralkanolyl and phenoxy-loweralkanolyl having phenoxy substituted by loweralkoxy, loweralkyl, nitro, amino, trifluoromethyl and halo;

$R_2$ is selected from hydrogen, hydroxy and loweralkyl, loweralkoxy or aryloxy;

$R_3$ is selected from loweralkanolyl, 4-cyanocycloalkyl-loweralkyl, phenoxy-loweralkanolyl and phenoxy-loweralkanolyl having phenoxy substituted by loweralkoxy, loweralkyl, nitro, amino, trifluoromethyl and halo;

$R_4$ is selected from hydrogen or loweralkyl,

X is selected from hydrogen, loweralkyl, loweralkoxy nitro, amino and halo, n is 1–3 inclusive.

Y is loweralkyl, m is 0 to 2 inclusive, and the pharmaceutically acceptable addition salts and hydrates thereof.

The hypotensive properties of the novel compounds of the present invention were determined by observing blood pressure of unanesthetized normotensive dogs or spontaneously hypertensive rats by standard procedures. In the rat tests, indwelling arterial catheters were placed either in the caudal artery or in the abdominal aorta and drugs were administered either intravenously or intra-arterially. These indwelling catheters were used for direct measurements of blood pressure for conscious animals using a Statham pressure transducer and recorded by a Grass polygraph.

It is accordingly an object of the present invention to provide novel 2-aryl-4-substituted quinazolines which have a high degree of hypotensive activity in animals and which exhibit a low degree of undesirable side effects.

Another object is to provide a novel method for the treatment of hypertensive living animals, especially mammalian animals for the purpose of lowering blood pressure.

Additional objects will be apparent to one skilled in the art and still other objects will become apparent hereinafter.

DETAILED DESCRIPTION OF THE INVENTION

The present invention encompasses the novel 2-aryl-4-substituted quinazolines as set forth hereinabove in Formula I and the definitions therewith as compositions of matter and the utilization of these novel compounds in pharmaceutical compositions in living animals for their pharmacological effect as set forth hereinabove and below.

The term "loweralkyl" as used in the specification and claims includes straight and branched chain radicals of up to eight carbon atoms inclusive and is exemplified by such groups as methyl, ethyl, propyl, isopropyl, butyl, tertiary butyl, amyl, isoamyl, hexyl, heptyl, octyl and the like.

By "loweralkenyl" is meant hydrocarbon chains up to 8 carbons having at least one double bond.

By "loweralkynyl" is meant hydrocarbon chains up to 8 carbons having at least one triple bond.

By "loweralkoxy" or "loweralkanyloxy" is meant —O—loweralkyl.

By "loweralkenyloxy" is meant —O—loweralkenyl.

By "loweralkynyloxy" is meant —O—loweralkynyl.

By "loweralkanolyl" is meant loweralkyl substituted by one or more hydroxy groups.

By "aryloxy" in the definition of $R_2$ is meant an aryl radical such as phenoxy or naphthoxy, preferably phenoxy.

Suitable pharmaceutically acceptable addition salts include such salts as hydrochloride, hydrobromide, sulfate phosphate, oxalate, citrate, tartrate, malate, maleate, fumarate and the like. Such salts are prepared by reacting the base dissolved in a suitable solvent with an equivalent amount of an appropriately suitable acid which causes precipitation of the addition salt. Conversely, the free base may be obtained from a given acid salt by neutralizing the salt in a suitable solvent with an equivalent amount of sodium hydroxide which causes the free base to precipitate.

To form a dimaleate salt of a piperazine derivative, twice the equivalent amount of maleic acid is used.

The following equation represents the reaction when compounds of the invention are prepared directly from 2-phenyl-4-chloroquinazoline in one step:

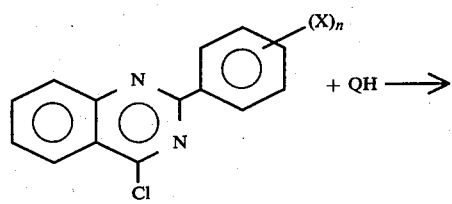

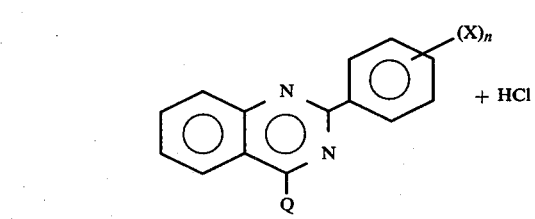

wherein Q, X and n are as defined hereinabove and QH is an appropriate primary or secondary amine and II is an appropriate 2-aryl-4-chloroquinazoline. All of the compounds may be prepared in this manner; however, it is sometimes advantageous to use alternate methods.

An alternate method particularly adaptable to preparation of compounds wherein Q is a heterocyclic amine residue involves first the reaction of compounds of Formula II with, for example, piperazine, methyl and dimethyl piperazine or 3-hydroxypyrrolidine or 3-hydroxypiperidine followed by expansion of the molecule by reaction of certain active groups R, $R_1$ and $R_2$,

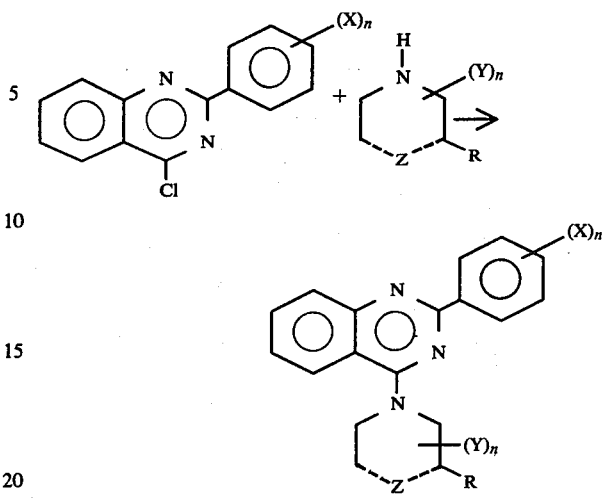

wherein $$Z = \left[ \begin{array}{c} \diagdown N \diagup \\ | \\ R_1 \end{array} \right]_p \text{ or } \left[ \begin{array}{c} \diagdown C \diagup \\ | \\ R_2 \end{array} \right]_p$$

and X, R, $R_1$, $R_2$ and n are as defined hereinabove. When the active group in the instances of R and $R_2$ is hydroxy, the chain may be expanded to an ether by reaction with an appropriate iodide. The reactive group in the instance of $R_1$=hydrogen may be expanded to a 4-substituted piperazine with an appropriate halide. Preparation 1 illustrates $R_1$=H and Example 8 illustrates the expansion to a 4-substituted piperazine.

When $R_1$ is hydrogen, conventional blocking agents such as acetyl chloride may be used to improve utilization of piperazinyl starting materials.

PREPARATION 1

4-(3,5-Dimethyl-1-piperazinyl)-2-phenylquinazoline Monohydrate

A mixture containing 12 g (0.05 mole) of 2-phenyl-4-chloroquinazoline, 5.7 g (0.05 mole) of 2,6-dimethylpiperazine and 250 ml of methanol was stirred at room temperature for 2 hrs, then refluxed for 6 hrs. The white crystalline precipitate which formed on standing at room temperature was identified as the hydrochloride salt of 4-(3,5-dimethyl-1-piperazinyl)-2-phenyl quinazoline. The salt was neutralized with sodium hydroxide to give the free base 4-(3-5-dimethyl-1-piperazinyl)-2-phenyl quinazoline which was then recrystallized from methanol and water to obtain the title compound in yield of 7.5 g, m.p. 122°–124° C.

Analysis: Calculated for $C_{20}H_{24}N_4O_1$: C,71.40; H,7.19; N,16.65 Found: C,71.04; H,6.92; N,16.11.

EXAMPLE 1

4-[[(2-Phenyl)-4-quinazolinyl)amino]methyl]cyclohexane carbonitrile

A mixture containing 6 g (0.025 mole) of 2-phenyl-4-chloroquinazoline, 4 g (0.029 mole) of 4-(aminomethyl)-cyclohexane carbonitrile and 150 ml isopropanol was refluxed for 2 hrs and filtered. The white crystalline solid from the filtration was recrystallized with methanol and water to give 3.3 g of the title compound, m.p. 190°–192° C.

Analysis: Calculated for $C_{22}H_{22}N_4$: C,77.16; H,6.48; N,16.36; Found: C,76.84; H,6.45; N,16.31.

EXAMPLE 2

1-(2-Phenyl-4-quinazolinyl)-4-piperidinol

A mixture containing 6 g (0.025 mole) of 2-phenyl-4-chloroquinazoline, 3.53 g (0.035 mole) of 4-hydroxypiperidine and 100 ml of 95% ethyl alcohol was refluxed for 3 hrs. One gram of sodium hydroxide (in one ml of water) was added and the mixture was refluxed for an additional 2 hr period. The mixture was filtered and the filtrate was added to 300 ml of water. The white crystalline precipitate was separated and recrystallized with methanol and water to give 3.2 g of the title compound, m.p. 165°–167° C.

Analysis: Calculated for $C_{19}H_{19}N_3O$: C,74.73; H,6.27; N,13.76; Found: C,74.72; H,6.31; N,13.72.

EXAMPLE 3

1-(2-Phenyl-4-quinazolinyl)-3-pyrrolidinol, Hemihydrate

A mixture containing 12 g (0.05 mole) of 2-phenyl 4-chloroquinazoline, 4.3 g (0.05 mole) of 3-hydroxy pyrrolidine and 150 ml of isopropanol was refluxed for 1½ hrs. The resulting reaction mixture was filtered. The filtrate was adjusted to pH 10 with sodium hydroxide and concentrated under reduced pressure to dryness. The semi-solid residue was recrystallized twice with hot water, a white crystalline solid was obtained. The white crystalline solid was dissolved in aqueous solution adjusted to pH=3 with hydrochloric acid and reprecipitated by adjusting to pH=7.5 using sodium hydroxide. This white crystalline solid was filtered and recrystallized with hot water to yield 7.3 g of the title compound, m.p. 180°–182° C.

Analysis: Calculated for $C_{36}H_{36}N_6O_3$: C,71.98; H,6.04; N,13.99; Found: C,72.36; H,5.72; N,14.08.

EXAMPLE 4

2-Methyl-2-[(2-phenyl-4-quinazolinyl)amino]-1-propanol

A mixture containing 12 g (0.05 mole) of 2 phenyl-4-chloroquinazoline, 4.5 g (0.05 mole) of 2-amino-2-methyl-1-propanol and 150 ml of isopropanol was refluxed for 4 hrs and filtered. The reaction mixture cooled to room temperature and filtered. The filtrate was concentrated to dryness under reduced pressure. The semi-solid residue was recrystallized with water to give 2.2 g of the title compound, m.p. 136°–138° C.

Analysis: Calculated for $C_{18}H_{19}N_3O$: C,73.70; H,6.53; N,14.32; Found: C,73.04; H,6.51; N,14.09.

EXAMPLE 5

4-(4-Hexyl-1-piperazinyl)-2-phenylquinazoline, Dihydrochloride, Dihydrate

A mixture containing 2.4 g (0.01 mole) of 2-phenyl-4-chloroquinazoline, 1.7 g (0.01 mole) of 1-n-hexyl piperazine and 150 ml of methanol was refluxed for 4 hrs. One half g of sodium hydroxide in one ml of water was added and refluxing continued for an additional 2 hr period. The oily precipitate in the reaction mixture was separated and washed with water to neutrality, dissolved in acetone and mixed with one ml of 12 N hydrochloric acid. The white crystalline solid obtained was recrystallized with acetone and methanol to give 3.2 g of the title compound, m.p. 272°–275° C.

Analysis: Calculated for $C_{24}H_{36}N_4O_2Cl_2$: C,59.62; H,7.50; N,11.59; Found: C,59.76; H,6.86; N,11.74.

EXAMPLE 6

1-(2-Phenyl-4-quinazolinyl)-3-piperidinemethanol

A mixture containing 12.3 g (0.05 mole) of 2-phenyl-4-chloroquinazoline, 5.75 g (0.05 mole) 3-(hydroxymethyl) piperidine and 200 ml isopropanol was refluxed for 1½ hrs. The resulting reaction mixture was filtered after standing at room temperature for 1½ hrs. The white crystalline solid obtained from the filtration was recrystallized with methanol and water to give 8.0 g of the title compound, m.p. 116°–118° C.

Analysis: Calculated for $C_{20}H_{21}N_3O$: C,75.21; H,6.63; N,13.16; Found: C,75.25; H,6.61; N,13.24.

EXAMPLE 7

4-[3-(2-Methoxyphenoxy)-1-pyrrolidinyl]-2-phenylquinazoline

To a solution containing 150 ml of isopropanol and 4.8 g (0.025 mole) of 3-o-methoxyphenoxypyrrolidine was added, with stirring, 6.15 g (0.025 mole) of 4-chloro-2-phenylquinazoline. The reaction was exothermic and the mixture refluxed for 15 min. The temperature subsided to room temperature and, after standing at room temperature for 1½ hr, the resulting reaction mixture was filtered. The crystalline solid was recrystallized with isopropanol. Yield of product was 1.9 g, m.p. 142°–144° C.

Analysis: Calculated for $C_{25}H_{23}N_3O_2$: C,75.54; H,5.83; N,10.57; Found: C,75.11; H,5.90; N,10.53.

EXAMPLE 8

3-Phenyl-4-[cis-2,5-dimethyl-4-(2-pyridinyl)-1-piperazinyl]quinazoline

A mixture containing 8.4 g (0.03 mole) of 2-phenyl-4-chloroquinazoline, 6.3 g (0.0335 mole) of 1-(2-pyridyl)-cis-2,5-dimethylpiperazine and 200 ml of isopropanol was refluxed for 6 hrs. The resulting reaction mixture was filtered after cooling to room temperature. A crystalline solid was obtained. The crude product was dissolved in 3 N hydrochloric acid and extracted with ether. The aqueous acidic solution was adjusted to pH=7.5 and filtered. Yield of crystalline solid was 4.3 g, m.p. 68°–70° C.

Analysis: Calculated for $C_{25}H_{25}N_5$: C,75.92; H,6.37; N,17.70; Found: C,75.30; H,6.33; N,17.66.

EXAMPLE 9

2-Phenyl-4-[4-(2-pyridinyl)-1-piperazinyl]quinazoline

A mixture containing 9.6 g (0.04 mole) of 2-phenyl-4-chloroquinazoline, 6.4 g. (0.04 mole) of 1-(2-pyridyl) piperazine and 250 ml of isopropanol was refluxed for 4 hrs. The resulting reaction mixture was filtered after cooling to room temperature. The crystalline solid was dissolved in 400 ml of 3 N hydrochloric acid and the aqueous acidic liquid was washed with ether. The aqueous layer was adjusted to pH=7.5 which precipitated crystalline solid. This acidification and basification were repeated once. Yield of product was 6.8 g, m.p. 164°–166° C. (air dried).

Analysis: Calculated for $C_{23}H_{21}N_5$: C,75.19; H,5.76; N,19.06; Found: C,75.13; H,5.72; N,19.15.

EXAMPLE 10

4-(2-Phenyl-4-quinazolinyl)-1-piperazineethanol Dihydrochloride, Monohydrate A mixture containing 6 g (0.025 mole) of 4-chloro-2-phenylquinazoline, 6 g (0.05 mole) of 1-hydroxyethyl-piperazine and 250 ml of methanol was refluxed for 6 hrs. The resulting reaction mixture was cooled to room temperature and poured into 500 ml of water. The gummy precipitate was separated and washed with water to neutrality then dissolved in 150 ml of acetone. To the acetone solution was added 4 ml of concentrated hydrochloric acid. The resulting white crystalline precipitate was filtered and washed with acetone. Yield of the dihydrochloride monohydrate salt was 8 g, m.p. 247°–276° C.

Analysis: Calculated for $C_{20}H_{26}N_4O_2Cl_2$: C,56.48; H,6.16; N,13.17; Found: C,56.67; H,5.73; N,13.30.

EXAMPLE 11

1-(2-Methoxyphenoxy)-3-[(2-phenyl-4-quinazolinyl)amino]-2-propanol, Monohydrate A mixture containing 5.8 g (0.025 mole) of 1-amino-3-ortho-methoxyphenoxy 2-propanol hydrochloride, 6 g (0.025 mole) of 2-phenyl-4-chloroquinazoline, 150 ml of methanol, 1.0 g of sodium hydroxide (in one ml of water) was refluxed for 6 hrs. Another one gram of sodium hydroxide (in one ml of water) was added and refluxing was continued for 2 hrs. The resulting reaction mixture was cooled to room temperature and filtered. The gummy substance which was obtained when the filtrate was mixed with 300 ml of water was separated, washed with water, then dissolved in acetone. The acetone solution was treated with one ml of 12 N hydrochloric acid and the white crystalline precipitate was separated, dissolved in water, adjusted to pH=7.5. A white crystalline solid was obtained. This crystalline solid was recrystallized with methanol and water to give 1.5 g of the title compound, m.p. 138°–140° C.

Analysis: Calculated for $C_{24}H_{25}N_3O_4$: C,68.72; H,6.01; N,10.02; Found: C,69.01; H,5.55; N,10.10.

EXAMPLE 12

4-(2-Phenyl-4-quinazolinyl)-α-[(2-propenyloxy)methyl]-1-piperazineethanol

A mixture containing 4.8 g (0.02 mole) of 2-phenyl 4-chloroquinazoline, 4 g (0.02 mole) of 1-(1-allyloxy-2-hydroxy)propyl piperazine and 100 ml of isopropanol was refluxed for 4 hrs. One ml of 50% sodium hydroxide was added and refluxing continued for one hour. The resulting reaction mixture was filtered. The filtrate was concentrated to dryness under reduced pressure. The oily residue solidified on standing at room temperature and was recrystallized twice with 400 ml hot water each time. Crystalline solid weighing 6.5 g was obtained, m.p. 85°–87° C.

Analysis: Calculated for $C_{24}H_{28}N_4O_2$: C,71.26; H,6.98; N,13.85; Found: C,71.67; H,7.04; N,13.77.

EXAMPLE 13

α-[(2-Methoxyphenoxy)methyl]-4-(2-phenyl-4-quinazolinyl)-1-piperazinepropanol, Dihydrochloride, Hemihydrate A mixture containing 4.8 g (0.02 mole) of 2-phenyl-4-chloro quinazoline, 5.6 g (0.02 mole) of 1-(3-hydroxy-4-ortho-methoxyphenoxy butyl)piperazine and 200 ml of methanol was refluxed for 16 hrs. One ml of 50% sodium hydroxide was added and refluxing continued for 4 hrs. The gummy substance which was obtained when the resulting reaction mixture was mixed with 300 ml of water was separated and dissolved in acetone. To the acetone solution was added 2 ml of 12 N hydrochloric acid. The resulting white crystalline precipitate was filtered off and recrystallized with acetone twice to give 3.8 g of the title compound, m.p. 215°–217° C.

Analysis: Calculated for $C_{58}H_{70}N_8O_7Cl_4$: C,61.48; H,6.22; N,9.89; Found: C,61.51; H,6.11; N,9.83.

EXAMPLE 14

2,6-Dimethyl-4-(2-phenyl-4-quinazolinyl)-α-[2-propenyloxy)-methyl]-1-piperazineethanol, Hemihydrate A mixture containing 3.18 g (0.01 mole) of 1-(2-phenyl quinazolinyl), 3.5-dimethylpiperazine, 1.14 g (0.01 mole) allyloxy glycidyl ether and 75 ml of isopropanol was refluxed overnight. The solution was concentrated to dryness under reduced pressure. The viscous oily residue was extracted with 150 ml of ether. The ether extract was concentrated to dryness. The solid residue was recrystallized with water to give 1.5 g of the title compound, m.p. 110°–112° C.

Analysis: Calculated for $C_{52}H_{66}N_8O_5$: C,70.72; H,7.53; N,12.69; Found: C,71.23; H,7.38; N,12.77.

EXAMPLE 15

1-(2-Ethoxyphenoxy)-3-[4-(2-phenyl-4-quinazolinyl)-1-piperazinyl]-2-propanol Dihydrochloride Monohydrate A mixture containing 3.6 g (0.015 mole) of 4-chloro-2-phenylquinazoline, 4.2 g (0.015 mole) of 1-(o-ethoxyphenyl-2-hydroxypropyl)piperazine and 150 ml of methanol was refluxed for 16 hr. One gram of sodium hydroxide (in 1 ml of water) was added and refluxing continued for 2 hrs. The resulting reaction mixture was cooled to room temperature and added into 350 ml of water. The gummy precipitate was washed to neutrality with water and dissolved in acetone then treated with 1 ml of concentrated hydrochloric acid. White crystalline precipitate was obtained, which was recrystallized with acetone. Yield of title compound was 3.8 g, m.p. 205°–207° C.

Analysis: Calculated for $C_{29}H_{36}N_4O_4Cl_2$: C,60.52; H,6.30; N,9.73; Found: C,60.74; H,6.00; N,9.78.

EXAMPLE 16

1-(4-Chloro-3-methylphenoxy)-3-[N-ethyl-N-(2-phenyl-4-quinazolinyl)amino]-2-propanol Dihydrochloride A mixture containing 6.6 g (0.025 mole) of 1-(3-methyl-4-chloro-phenoxy)-2-hydroxypropyl-N-ethyl amine, 6 g (0.025 mole) of 4-chloro-2-phenyl-quinazoline and 50 ml of dimethyl formamide was heated at 60°–80° C. with stirring for 6 hrs. After cooling to room temperature, 2 ml of 50% NaOH was added. This basic mixture was heated for 2 hrs at 60°–80° C. The resulting mixture was added into one liter of water. The gummy precipitate was separated, dissolved in acetone, and dried over sodium sulfate. The acetone solution was treated with ethereal hydrogen chloride and the dihydrochloride acid salt was separated and recrystallized with acetone. Yield was 4.5 g, m.p. 90°–92° C.

Analysis: Calculated for $C_{26}H_{28}N_3O_2Cl_3$: C,59.95; H,5.41; N,8.07; Found: C,60.44; H,5.29; N,8.12.

EXAMPLE 17

1-(3,5-Dimethylphenoxy)-3-[(2-phenylquinazolin-4-yl)amino]-2-propanol

A mixture of 12 g (0.05 mole) of 4-chloro-2-phenylquinazoline, 10.0 g (0.05 mole) of 1-[(3,5-dimethylphenoxy)-3-amino]-2-propanol and 250 ml of dimethylformamide was heated with stirring for 18 hrs at 75°–80° C. 15 ml of 6 N sodium hydroxide was added followed by addition of 600 ml of water. The solid which precipitated was separated by filtration and washed with water to neutrality of the wash. The filter cake was triturated with acetone and petroleum ether. The semi-solid was separated by decantation and allowed to stand in low boiling petroleum ether at room temperature until it solidified and was recrystallized from acetone and diethyl ether. The product which weighed 8.2 g melted at 170°–172° C.

Analysis: Calculated for $C_{25}H_{25}N_3O_2$: C,75.16; H,6.31; N,10.52; Found: C,74.85; H,6.29; N,10.52.

EXAMPLE 18

1-Phenoxy-3-[(2-phenyl-4-quinazolin-4-yl)amino]-2-propanol

A mixture of 2.4 g (0.01 mole) of 4-chloro-2-phenylquinazoline, 1.65 g (0.01 mole) of 1-phenoxy-3-amino-2-propanol, 100 ml of dimethylformamide and 0.04 g (0.01 mole) of sodium hydroxide was heated with stirring at 75° C. For 6 hrs, then cooled to room temperature. The mixture was poured into 1 liter of water which resulted in precipitation of white crystals. This latter step was exothermic. The solid was filtered off and recrystallized with acetone and ether. The weight of product was 2.1 g, m.p.

Analysis: Calculated for $C_{23}H_{21}N_3O_2$: C,74.37; H,5.70; N,11.31; Found: C,74.53; H,5.40; N,11.61.

EXAMPLE 19

4-[4-(Naphthoxy)piperidinyl]-2-phenylquinazoline

Equimolar quantities of 4-(4-hydroxypiperidinyl)-2-phenylquinazoline, sodium hydride and 1-fluoronaphthalene are heated in dimethylformamide to prepare the title compound.

EXAMPLE 20

4-(4-Phenoxypiperidinyl)-2-phenylquinazoline

Equimolar quantities of 4-(4-hydroxypiperidinyl-2-phenylquinazoline, sodium hydride, and fluorobenzene are heated in dimethylformamide to prepare the title compound.

EXAMPLE 21

4-(4-Ethoxypiperidine)-2-phenylquinazoline

Equimolar amounts of 4-(4-hydroxypiperidinyl)-2-phenylquinazoline, sodium hydride, and ethyl fluoride are reacted in dimethylformamide to prepare the title compound.

EXAMPLE 22

4-(3-Butoxypiperidinyl)-2-phenylquinazoline

Equimolar amounts of 4-(3-hydroxypiperidinyl-2-phenylquinazoline and soda amide are mixed in dimethylformamide and reacted with butyl chloride to prepare the title compound.

EXAMPLE 23

4-(2-Phenyl-4-quinazolinyl)-α-[(2-propargyloxy)methyl]-1-piperazineethanol

Utilizing the procedure of Example 12 but substituting an equimolar amount of 1-(1-propargyloxy-2-hydroxy)propyl piperazine for 1-(1-allyloxy-2-hydroxy)propyl piperazine, the title compound is obtained.

EXAMPLE 24

4-(2-Phenyl-4-quinazolinyl)-α-[(propyloxy)methyl]-1-piperazinethanol

The title compound is obtained by hydrogenating over Raney nickel 4-(2-phenyl-4-quinazolinyl)-α-[(2-propargyloxy)methyl]-1-piperazineethanol.

FORMULATION AND ADMINISTRATION

Useful compositions containing at least one of the compounds according to the invention in association with a pharmaceutical carrier or excipient may be prepared in accordance with conventional technology and procedures. Thus, the compounds may be presented in a form suitable for oral or parenteral administration. For example, compositions for oral administration can be solid of liquid and can take the form of capsules, tablets, coated tablets and suspensions, such compositions comprising carriers or excipients conveniently used in the pharmaceutical art. Suitable tableting excipients include lactose, potato, and maize starches, talc, gelatin, and stearic, and silicic acids, magnesium stearate, and polyvinyl pyrrolidone.

For parenteral administration the carrier or excipient may be a sterile, parenterally acceptable liquid; e.g., water or a parenterally acceptable oil; e.g., arachis oil contained in ampules.

Advantageously, the compositions may be formulated as dosage units, each unit being adapted to supply a fixed dose of active ingredients. Tablets, capsules, coated tablets and ampules are examples of preferred dosage unit forms according to the invention. Each dosage unit adapted for oral administration can conveniently contain 5 to 250 mg and preferably 20 to 200 mg of the active ingredient, whereas each dosage unit adapted for intramuscular administration can conveniently contain 5 to 100 mg and preferably 10 to 75 mg of the active ingredient. Daily oral dosages of 10 to 500 mg are anticipated, depending on the severity of the condition being treated and size of the host.

It is only necessary that the active ingredient constitute an effective amount; i.e., such that a suitable effective dosage will be obtained consistent with the dosage form employed. The exact individual dosages as well as daily dosages will, of course, be determined according to standard medical principles under the direction of a physician or veterinarian.

The following formulations are representative for all of the pharmacologically active compounds of the invention.

1. Capsules—capsules of 5, 25 and 50 mg of active ingredient per capsule are prepared. With the higher amounts of active ingredient, reduction may be made in the amount of lactose.

| Typical blend for encapsulation | Per Capsule, mg. |
|---|---|
| Active ingredient | 5.0 |
| Lactose | 296.7 |

11
-continued

| Typical blend for encapsulation | Per Capsule, mg. |
|---|---|
| Starch | 129.0 |
| Magnesium stearate | 4.3 |
| Total | 435.0 mg. |

2. Tablets—A typical formulation for a tablet containing 5 mg of active ingredient per tablet follows. The formulation may be used for other strengths of active ingredient by adjustment of weight of dicalcium phosphate.

| | Per Tablet, mg. |
|---|---|
| 1. Active ingredient | 5.0 |
| 2. Corn starch | 13.6 |
| 3. Corn starch (paste) | 3.4 |
| 4. Lactose | 79.2 |
| 5. Dicalcium phosphate | 68.2 |
| 6. Calcium stearate | 0.9 |
| Total | 170.3 mg. |

Uniformly blend 1, 2, 4 and 5. Prepare 3 as a ten percent paste in water. Granulate the blend with starch paste and pass the wet mass through an eight-mesh screen. The wet granulation is dried and sized through a twelve-mesh screen. The dried granules are blended with the calcium stearate and compressed.

Additional tablet formulations preferably contain a higher dosage of the active ingredient and are as follows:

| 50 mg. Tablet | |
|---|---|
| Ingredients | Per Tablet, mg. |
| Active ingredient | 50.0 |
| Lactose | 90.0 |
| Milo starch | 20.0 |
| Corn starch | 38.0 |
| Calcium stearate | 2.0 |
| Total | 200.0 mg. |

Uniformly blend the active ingredient, lactose, starches, and dicalcium phosphate when present. The blend is then granulated using water as a granulating medium. The wet granules are passed through an eight-mesh screen and dried at 140°–160° F. overnight. The dried granules are passed through a ten-mesh screen, blended with the proper amount of calcium stearate, and the lubricated granules then converted into tablets on a suitable tablet press.

3.

| Injectable - 2% sterile solution | Per cc |
|---|---|
| Active ingredient | 20 mg. |
| Preservative, e.g., chlorobutanol | 0.5% weight/volume |
| Water for injection | q.s. |

Prepare solution, clarify by filtration, fill into vials, seal, and autoclave.

Various modifications in the compounds, compositions and methods of the invention will be apparent to one skilled in the art and may be made without departing from the spirit or scope thereof, and it is therefore to be understood that the invention is to be limited only by the scope of the appended claims.

What is claimed is:

12

1. The method of treating hypertension in warm blooded animals which comprises administering to said animal an effective amount of a compound having the formula:

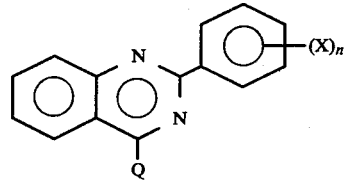

wherein
Q is

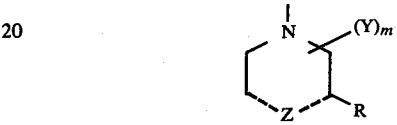

or $-NR_3R_4$

R is selected from hydrogen, hydroxy, loweralkoxy, loweralkanolyl, phenoxy or phenoxy substituted by loweralkyl, loweralkoxy, trifluoromethyl, amino, nitro or halo;

Z is selected from

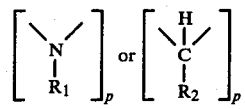

and p is zero to one inclusive;

$R_1$ is selected from loweralkyl, loweralkanolyl, 2-pyridyl, loweralkenyloxy-loweralkanolyl, loweralkynyloxyloweralkanolyl, loweralkanyloxy-loweralkanolyl, phenoxyloweralkanolyl and phenoxy-loweralkanolyl having phenoxy substituted by loweralkoxy, loweralkyl, nitro, amino, trifluoromethyl and halo;

$R_2$ is selected from hydrogen, hydroxy, loweralkyl, loweralkoxy, phenoxy or naphthoxy;

$R_3$ is selected from loweralkanolyl, 4-cyanocyclohexylloweralkyl, phenoxy-loweralkanolyl or phenoxy-loweralkanolyl having phenoxy substituted by loweralkoxy, loweralkyl, nitro, amino, trifluoromethyl or halo;

$R_4$ is selected from hydrogen or loweralkyl;

X is selected from hydrogen, loweralkyl, loweralkoxy, nitro, amino or halo and n is one to three;

Y is loweralkyl and m is 0 to 2 inclusive and the pharmaceutically acceptable addition salts and hydrates thereof.

2. The method of claim 1 herein the compound is 2-methyl-2-[(2-phenyl-4-quinazolinyl)-amino]-1-propanol.

3. The method of claim 1 wherein the compound is 4-(4-hexyl-1-piperazinyl)-2-phenylquinazoline.

4. The method of claim 1 wherein the compound is 1-(2-phenyl-4-quinazolinyl)-3-piperidinemethanol.

5. The method of claim 1 wherein the compound is 4-[3-(2-methoxyphenoxy)-1-pyrrolidinyl]-2-phenylquinazoline.

6. The method of claim 1 wherein the compound is 2-phenyl-4-[4-(2-pyridinyl)-1-piperazinyl]quinazoline.

7. The method of claim 1 wherein the compound is 4-(2-phenyl-4-quinazolinyl)-1-piperazine ethanol.

8. The method of claim 1 wherein the compound is 4-(2-phenyl-4-quinazolinyl)-α-[(2-propenyloxy)methyl]-1-piperazine ethanol.

9. A pharmaceutical composition for treating hypertension in warm-blooded animals for the purpose of lowering blood pressure comprising (a) an effective amount of a compound selected from the group consisting of 4-(4-hexyl-1-piperazinyl)-2-phenylquinazoline, 1-(2-phenyl-4-quinazolinyl)-3-piperidinemethanol, 4-[3-(2-methoxyphenoxyl-1-pyrrolidinyl]-2-phenylquinazoline, 2-phenyl-4-[4-(2-pyridinyl)-1-piperazinyl]quinazoline and 4-(2-phenyl-4-quinazolinyl-α-[(2-propenyloxy)-methyl]-1-piperazineethanol and (b) a pharmaceutically acceptable carrier therefor.

10. The pharmaceutical composition of claim 9 wherein the compound is 4-(4-hexyl-1-piperazinyl)-2-phenylquinazoline.

11. The pharmaceutical composition of claim 9 wherein the compound is 1-(2-phenyl-4-quinazolinyl)-3-piperidinemethanol.

12. The pharmaceutical composition of claim 9 wherein the compound is 4-[3-(2-methoxyphenoxyl-1-pyrrolidinyl]-2-phenylquinazoline.

13. The pharmaceutical composition of claim 9 wherein the compound is 2-phenyl-4-[4-(2-pyridinyl)-1-piperazinyl]quinazoline.

14. The pharmaceutical composition of claim 9 wherein the compound is 4-(2-phenyl-4-quinazolinyl)-α-[(2-propenyloxy)methyl]-1-piperazineethanol.

* * * * *